United States Patent
Kuen

(12) 
(10) Patent No.: US 6,627,788 B1
(45) Date of Patent: Sep. 30, 2003

(54) SWIMWEAR WITH WATER DRAIN

(75) Inventor: David Arthur Kuen, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 324 days.

(21) Appl. No.: 09/698,346

(22) Filed: Oct. 27, 2000

(51) Int. Cl.$^7$ ................................................ A61F 13/15
(52) U.S. Cl. ...................................................... 604/364
(58) Field of Search ................................. 604/364, 365, 604/366, 367, 375, 386, 387, 389, 385.01, 395

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,502,538 A | 3/1970 | Petersen | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| 4,062,451 A | 12/1977 | Gander | |
| 4,333,465 A | 6/1982 | Wiegner | |
| 4,340,563 A | 7/1982 | Appel et al. | |
| 4,663,220 A | 5/1987 | Wisneski et al. | |
| 4,704,116 A | 11/1987 | Enloe | |
| 4,790,836 A | 12/1988 | Brecher | |
| 4,940,464 A | 7/1990 | Van Gompel et al. | |
| 5,046,272 A | 9/1991 | Vogt et al. | |
| 5,104,116 A | 4/1992 | Pohjola | |
| 5,224,405 A | 7/1993 | Pohjola | |
| 5,226,992 A | 7/1993 | Morman | |
| 5,236,428 A | 8/1993 | Zajaczkowski | |
| 5,300,358 A | 4/1994 | Evers | |
| 5,303,424 A | 4/1994 | Cromartie | |
| 5,330,459 A | 7/1994 | Lavon et al. | |
| 5,384,189 A | 1/1995 | Kuroda et al. | |
| 5,509,913 A | 4/1996 | Yeo | |
| D377,980 S | * 2/1997 | Slingland | ................... D24/126 |
| 5,674,213 A | 10/1997 | Sauer | |
| 5,681,299 A | 10/1997 | Brown | |
| 5,792,132 A | * 8/1998 | Garcia | ................... 604/385.01 |
| 5,876,393 A | 3/1999 | Ahr et al. | |
| 5,885,264 A | 3/1999 | Matsushita | |
| 2002/0082572 A1 | * 6/2002 | Wehner et al. | ............... 604/364 |
| 2002/0095129 A1 | * 7/2002 | Friderich et al. | ...... 604/385.28 |

FOREIGN PATENT DOCUMENTS

| | | | |
|---|---|---|---|
| EP | 217 032 | 2/1992 | |
| EP | 0 745 367 | 5/1996 | |
| WO | WO 9603950 A1 | * 2/1996 | ........... A61F/13/15 |
| WO | WO 98/44883 | 10/1998 | |
| WO | WO 00/38751 | 7/2000 | |
| WO | WO 00/39378 | 7/2000 | |
| WO | WO 0234187 A1 | * 5/2002 | ........... A61F/13/15 |

* cited by examiner

Primary Examiner—John J. Calvert
Assistant Examiner—Angela Grayson
(74) Attorney, Agent, or Firm—Pauley Petersen Kinne & Erickson

(57) ABSTRACT

An absorbent swimwear garment having a water drain in the crotch area. A drain opening of the water drain is covered with a urine insoluble, water soluble material, thereby remaining sealed for initial product use prior to swimming. During initial product use, the absorbent swimwear garment is able to contain urine and bowel movements, just like ordinary diapers and training pants. When the swimwear garment is submersed in swim water, such as pool or lake water, the water soluble material becomes soluble and "opens" the drain, allowing swim water, but not bowel movements, to drain out the bottom of the garment.

40 Claims, 4 Drawing Sheets

SWIMWEAR WITH WATER DRAIN

FIELD OF THE INVENTION

This invention is directed to swimpants and swimsuits for pre-toilet trained children. More particularly, the swimwear has a water drain for draining swim water from the garment.

BACKGROUND OF THE INVENTION

Absorbent swim pants and swimsuits for pre-toilet trained children have absorbent cores and moisture barriers to prevent leaks of urine and bowel movements. Because the products are designed for leakage prevention, they retain sizable quantities of swim water, such as pool or lake water, during and after swimming. This retention of water is undesirable because it causes the pants to sag down, is uncomfortable for the wearer, and can soak towels and clothing after swimming.

There is a need or desire for an absorbent swimwear garment that provides uncompromised urine and bowel movement containment before swimming and allows the draining of excess water from the garment during and after swimming.

SUMMARY OF THE INVENTION

The present invention is directed to a pant-like absorbent swimwear garment, having a water drain for draining swim water, such as pool or lake water, from the garment. The water drain includes urine insoluble, water soluble material, suitably located in the crotch area of the pant. The drain opening is sealed shut with this material during initial product use, prior to swimming. The drain opening remains shut, even when the wearer releases urine or bowel movements, prior to swimming. After the swimpant is submerged in swim water, the water soluble material dissolves and "opens" the drain, allowing pool water, but not bowel movements or other solids, to drain out the bottom of the swimpant.

The urine insoluble, water soluble material can be a material whose solubility is temperature dependent. For example, the material can be insoluble in aqueous fluids, such as bodily fluids, above a specified temperature, for example 25 degrees Celsius (77 degrees Fahrenheit), but soluble in aqueous fluids, such as swim water, at less than the specified temperature, for example 25 degrees Celsius. Other non-temperature dependent materials that are urine insoluble and water soluble include materials whose solubility is determined by pH of the water, enzyme catalysis, borate ion concentration and salt sensitive binders.

The urine insoluble, water soluble material can be in the form of a film or tape covering the drain opening. The drain opening can be in the form of holes, cuts or seams in the crotch area of the swimpant's moisture barrier material(s) or containment flaps. The tape or film is suitably applied on the inside surface of the swimpant moisture barrier, between an outer cover and an absorbent layer, to reduce chances of being accidentally solubilized by perspiration or other small quantities of liquid. Alternatively, the tape or film can be applied to the outer surface of the outer cover.

Prior to swimming, the film covers the drain opening and the swimpant contains urine and bowel movements like a typical diaper or training pant. When the pant is worn while swimming in typical swimming temperature water below the specified temperature, for instance about 25 degrees Celsius, the swim water cools and dilutes any urine that may be present and solubilizes the film covering the drain openings. After being submerged in swim water for a length of time, the drains are open and excess water and urine not held in the absorbent material flow out the pant through the opened drains. Bowel movement material is kept inside the pant regardless of whether the drains are open or closed because the liner and the absorbent material are constructed as in a normal absorbent garment to keep bowel movements contained.

The resulting product is an absorbent swimwear garment that provides uncompromised urine and bowel movement containment before swimming but allows the draining of excess water from the swimpant after swimming. Bowel movement containment is not substantially altered before or after swimming.

With the foregoing in mind, it is a feature and advantage of the invention to provide an absorbent swimwear garment with water drains.

DEFINITIONS

Figure 1:
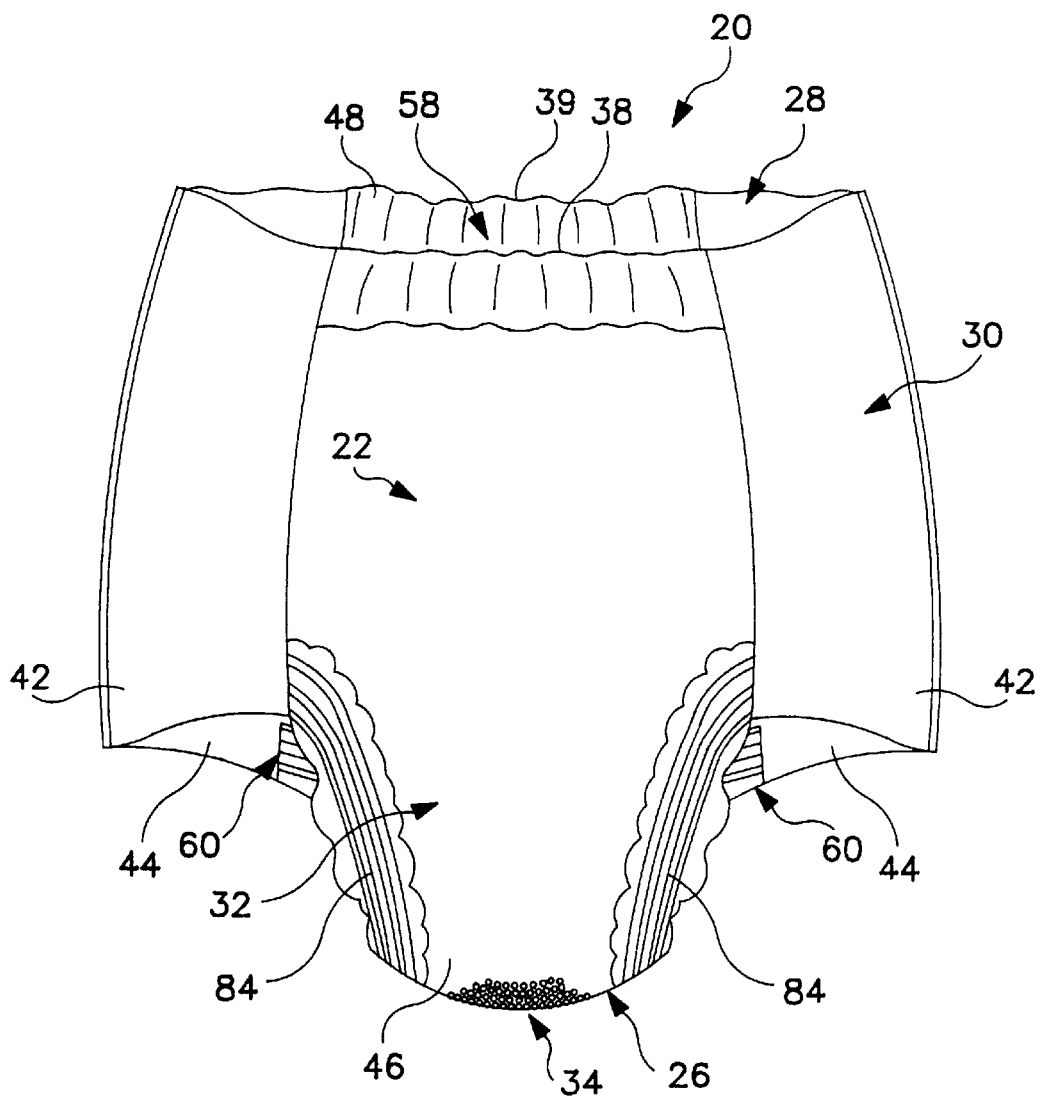
FIG. 1 is a front perspective view of an absorbent swimpant.

Within the context of this specification, each term or phrase below will include the following meaning or meanings.

"Drain" refers to one or more passages designed for liquids to pass through a liquid barrier material.

"Elastic," "elasticized" and "elasticity" mean that property of a material or composite by virtue of which it tends to recover its original size and shape after removal of a force causing a deformation.

"Film" refers to a thermoplastic film made using a film extrusion and/or foaming process, such as a cast film or blown film extrusion process. The term includes apertured films, slit films, and other porous films which constitute vapor transfer films, as well as films which do not transfer liquid, including liquid-impermeable, vapor-permeable films.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

"Layer" when used in the singular can have the dual meaning of a single element or a plurality of elements.

"Liquid impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Liquid-permeable material" or "liquid water-permeable material" refers to a material present in one or more layers, such as a film, nonwoven fabric, or open-celled foam, which is porous, and which is water permeable due to the flow of water and other aqueous liquids through the pores. The pores in the film or foam, or spaces between fibers or filaments in a nonwoven web, are large enough and frequent enough to permit leakage and flow of liquid water through the material.

"Meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self-bonding when deposited onto a collecting surface. Meltblown fibers used in the present invention are preferably substantially continuous in length.

"Nonwoven" and "nonwoven web" refer to materials and webs of material which are formed without the aid of a textile weaving or knitting process.

"Opening" refers to one or more holes, gaps in a seam, cuts, or slits.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. No. 3,338,992 and U.S. Pat. No. 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Surface" includes any layer, film, woven, nonwoven, laminate, composite, or the like, whether pervious or impervious to air, gas, and/or liquids.

"Thermoplastic" describes a material that softens when exposed to heat and which substantially returns to a non-softened condition when cooled to room temperature.

These terms may be defined with additional language in the remaining portions of the specification.

DETAILED DESCRIPTION OF THE PRESENTLY PREFERRED EMBODIMENTS

The present invention is directed to an absorbent swimwear garment having a water drain for draining excess water, such as pool or lake water, from the garment after swimming. The principles of the present invention can be incorporated into disposable, pant-like, absorbent swimwear articles, such as swimpants and swimsuits.

Figure 2:
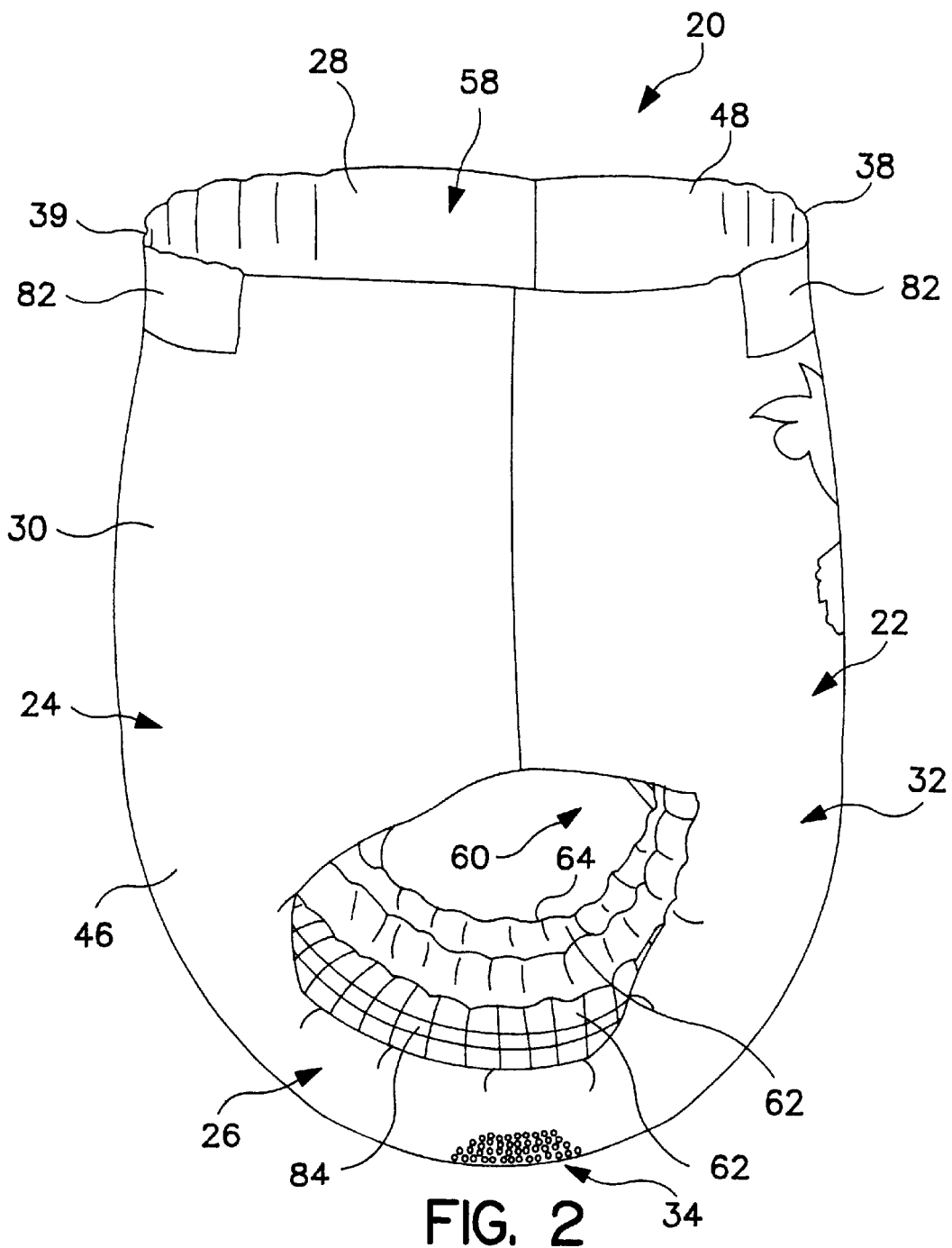
FIG. 2 is a side perspective view of an absorbent swimpant.

Referring to FIGS. 1 and 2, an absorbent swimpant 20 is illustrated. The swimpant 20 includes an absorbent chassis 32. The absorbent chassis 32 defines a front region 22, a back region 24, a crotch region 26 interconnecting the front and back regions, an inner surface 28 which is configured to contact the wearer, and an outer surface 30 opposite the inner surface which is configured to contact a pool or lake environment. A water drain 34 is located on the outer surface 30 in the crotch region 26 of the absorbent chassis 32.

Figure 3:
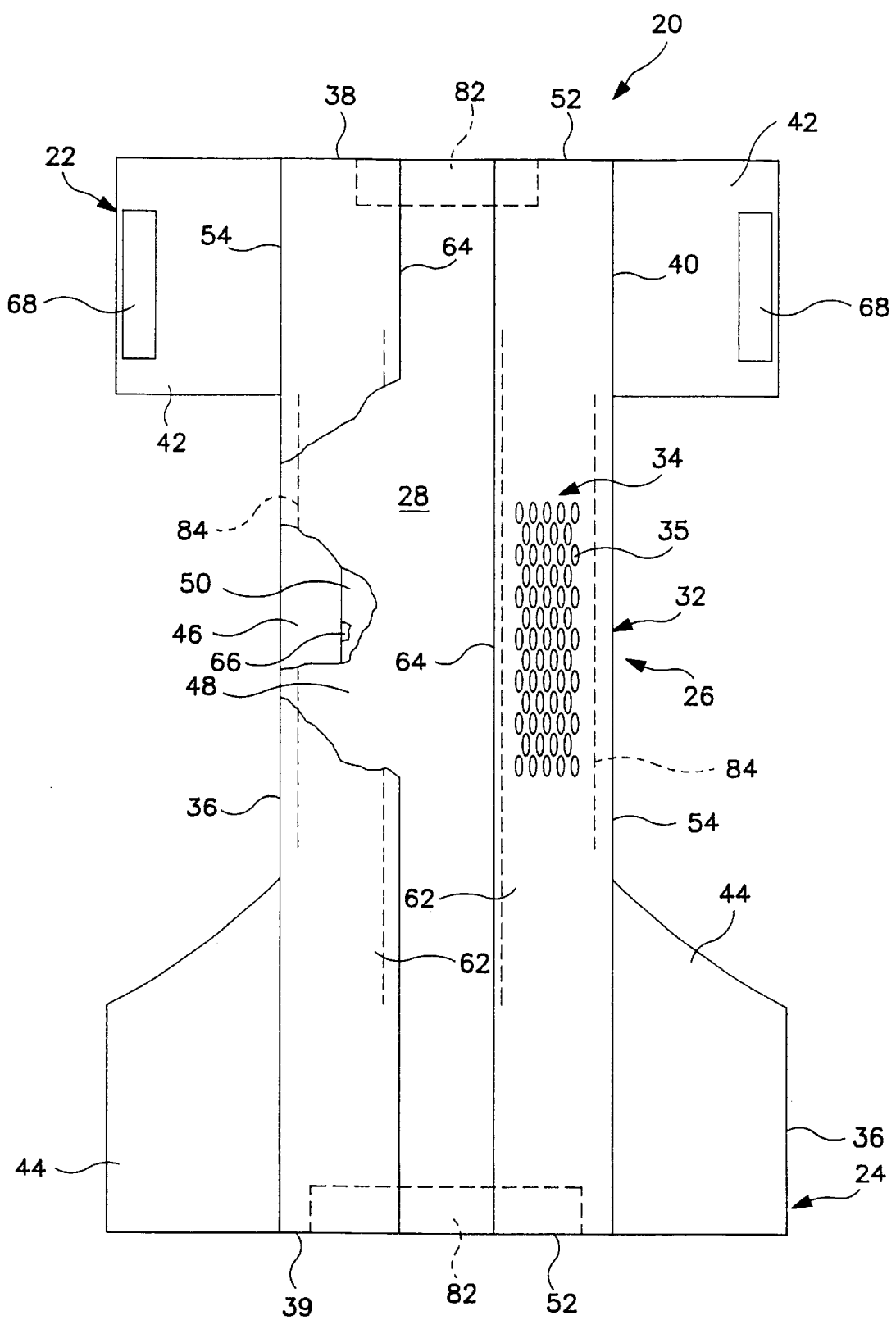
FIG. 3 is a plan view of an absorbent swimpant in a partially disassembled, stretched flat state, and showing the surface of the swimpant that faces the wearer when the swimpant is worn, and with portions cut away to show the underlying features.

Referring to FIG. 3, the swimpant 20 is shown in a partially disassembled, stretched flat state, showing the inner surface 28 which faces the wearer when the garment is worn. As shown, the absorbent chassis 32 also defines a pair of transversely opposed side edges 36 and a pair of longitudinally opposed waist edges, which are designated front waist edge 38 and back waist edge 39. The front region 22 is contiguous with the front waist edge 38, and the back region 24 is contiguous with the back waist edge 39. The chassis 32 also includes a somewhat rectangular composite structure 40, a pair of transversely opposed front side panels 42, and a pair of transversely opposed back side panels 44. The composite structure 40 and side panels 42 and 44 may be integrally formed, as shown in FIG. 2, or may include two or more separate elements, as shown in FIGS. 1 and 3.

The illustrated composite structure 40 includes an outer cover 46, a body side liner 48 which is connected to the outer cover 46 in a superposed relation, and an absorbent assembly 50 which is located between the outer cover 46 and the body side liner 48. The rectangular composite structure 40 has opposite linear end edges 52 that form portions of the front and back waist edges 38 and 39, and opposite linear, or curvilinear, side edges 54 that form portions of the side edges 36 of the absorbent chassis 32.

As shown in the swimpants 20 in FIGS. 1 and 2, the front and back regions 22 and 24 together define a three-dimensional pant configuration having a waist opening 58 and a pair of leg openings 60. The waist edges 38 and 39 of the absorbent chassis 32 are configured to encircle the waist of the wearer when worn and provide the waist opening 58 which defines a waist perimeter dimension. Portions of the transversely opposed side edges 36 (FIG. 3) in the crotch region 26 generally define the leg openings 60. The front region 22 includes the portion of the swimpant 20 which, when worn, is positioned on the front of the wearer while the back region 24 includes the portion of the swimpant 20 which, when worn, is positioned on the back of the wearer. The crotch region 26 of the swimpant 20 includes the portion of the swimpant 20 which, when worn, is positioned between the legs of the wearer and covers the lower torso of the wearer.

The absorbent chassis 32 is configured to contain and/or absorb any body exudates discharged from the wearer. For example, the absorbent chassis 32 can include a pair of elasticized containment flaps 62 (shown in FIGS. 2 and 3) which are configured to provide a barrier to the transverse flow of body exudates. The elasticized containment flaps 62 define an unattached edge 64 which assumes an upright, generally perpendicular configuration in at least the crotch region 26 of the swimpant 20 to form a seal against the wearer's body. Suitable constructions and arrangements for the containment flaps 62 are generally well known to those skilled in the art and are described in U.S. Pat. No. 4,704,116 issued Nov. 3, 1987 to Enloe, which is incorporated herein by reference.

Absorbent swimwear is designed for leakage prevention. Thus, when a wearer wears absorbent swimwear into a pool or lake, the swimwear has a tendency to fill up with water in the crotch region 26. Therefore, the water drain 34 is designed to "open" when the swimpant 20 is submerged in swim water, such as pool or lake water. A layer of urine insoluble, water soluble material 66 is used to seal the water drain 34 for initial product use. As used herein, the term "water soluble material" includes swim water softenable or water weakened material, such as a material that becomes a gel in water, that can be pushed through the water drain 34 by water pressure inside the swimpant 20. When the water drain 34 is sealed, the swimpant 20 works similar to regular diapers and training pants, absorbing any urine and containing any bowel movements excreted by the wearer. Because the material 66 is urine insoluble, the water drain 34 remains sealed even when exposed to urine, as long as the swimpant 20 is not submerged in water.

When the swimpant 20 is submerged in water for a length of time, such as when a wearer is swimming or wading in a pool or a lake, the water soluble material 66 becomes at least partially soluble and "opens" the water drain 34, allowing excess water and urine not held in the absorbent assembly 50 to flow out the swimpant 20 through a drain opening 35. Bowel movement material is kept inside the swimpant 20 regardless of whether the drain 34 is open or closed, because the body side liner material 48 is constructed as in a normal absorbent garment, such as a diaper or training pant, to keep bowel movements contained.

Figure 4:
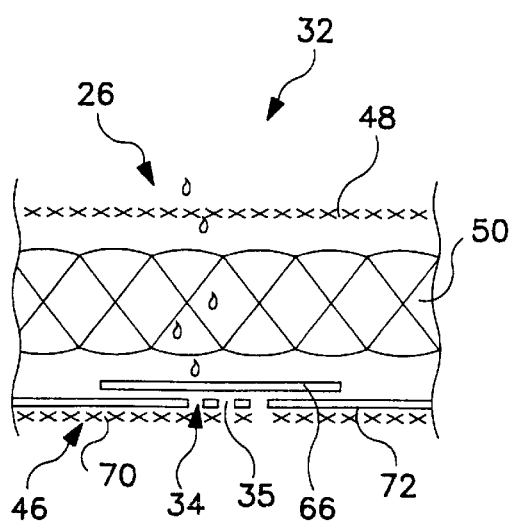
FIG. 4 is a cross-sectional view of the composite chassis of the swimpant before swimming.
Figure 5:
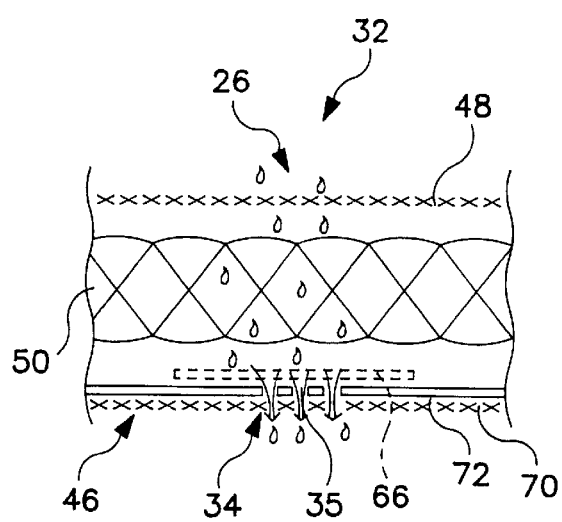
FIG. 5 is a cross-sectional view of the composite chassis of the swimpant during or after swimming, when the drain is open.

FIG. 4 shows a cross-sectional view of the crotch region 26 of the composite chassis 32 of the swimpant 20 before swimming. The body side liner 48 is situated adjacent the wearer's skin when the swimpant 20 is worn. Fluids, i.e., urine, can flow through the body side liner 48 and are then absorbed into the absorbent assembly 50. The outer cover 46 is substantially liquid impermeable, such that substantially all fluids originating within the swimpant 20 stay within the swimpant 20, at least prior to swimming. The urine insoluble, water soluble material 66 is between the absorbent assembly 50 and the outer cover 46. The location of the urine insoluble, water soluble material 66 is away from the liquid permeable body side liner 48 to reduce any chance of being accidentally solubilized by perspiration or other small quantities of water. The material 66 can be in the form of a film or tape, covering the drain opening 35 of the water drain 34. FIG. 5 shows a cross-sectional view of the crotch region 26 of the composite chassis 32 of the swimpant 20 during or after swimming, when the drain 34 is open. The body side liner 48, absorbent assembly 50, material 66, and outer cover 46 can be joined together by any suitable means, such as adhesives, as is well known in the art.

The drain opening 35 of the water drain 34 can include openings in the form of holes, cuts, slits or gaps in seams in the outer surface 30 of the crotch region 26. The water drain 34 can be located in the outer cover 46, as shown in FIGS. 1 and 2, or in the containment flaps 62, as shown in FIG. 3. If the water drain 34 is located in the containment flaps 62, the drain opening 35 is ideally covered with a permeable material, such as spunbond, to prevent bowel movements from escaping through the drain opening 35.

The water drain 34 covers roughly 0.01 $cm^2$ to about 250 $cm^2$ of the outer surface 30 of the chassis 32, suitably 0.5 $cm^2$ to 100 $cm^2$, more suitably 1 $cm^2$ to 10 $cm^2$. However, if the drain opening 35 is in the form of slits, the water drain 34 then covers essentially no surface area of the outer surface 30 of the chassis 32. The urine insoluble, water soluble material 66 covering the drain opening 35 is generally 0.005 mm to about 0.5 mm thick, suitably 0.01 mm to 0.037 mm thick, more suitably 0.012 mm to 0.025 mm thick. When the swimpant 20 is worn while swimming, the water dilutes any urine that may be present and solubilizes the material 66 covering the drain opening 35, thereby allowing the excess water within the swimpant 20 to drain out while still maintaining any bowel movements within the swimpant 20.

Solubility of the urine insoluble, water soluble material 66 can be dependent on any of a number of factors, including temperature, pH of the water, enzyme catalysis, borate ion concentration, and salt sensitive binders. One example of a temperature dependent, urine insoluble, water soluble material is described in U.S. Pat. No. 5,509,913 issued to Richard Yeo, incorporated herein by reference. The material 66, as used herein, suitably includes any of the following polymers: polyvinyl methyl ether, polyethyl oxazoline, polyvinyl pyrrolidone, hydroxy propyl cellulose, and polyvinyl alcohol having a percent hydrolysis of less than about 75%. A preferred polymer is polyvinyl alcohol, available under the trade name GOHSENOL® Nippon Synthetic Chemical Industry Co., Ltd., of Osaka, Japan, with suitable grades including KZ-06, LL-02, and KH-17. Any of these polymers can be used in combination with a sulfate, citrate, phosphate, or chromate salt anion to make the polymer insoluble in body fluids above 25 degrees Celsius but soluble in tap water below 25 degrees Celsius. Thus, when the swimpant 20 is worn while swimming in typical swimming temperature water below about 25 degrees Celsius (77 degrees Fahrenheit) the water dilutes any urine that may be present and solubilizes the material 66 covering the drain opening 35. This solubility temperature can be adjusted chemically.

One example of a urine insoluble, water soluble material 66 whose solubility is dependent on pH of the water includes a pH sensitive gelled polymer. The pH sensitive gelled polymeric material is stored in the presence of a separate acid pH solution. When the material is placed in a large quantity of neutral pH water, it disintegrates as a result of the pH shift.

Another example of a urine insoluble, water soluble material 66 mentioned is material that is susceptible to attack by specific enzyme catalysis that breaks down the structural integrity of the material. In such material, the enzymes may be introduced into the water, such as rinse-off water, separately.

One example of urine insoluble, water soluble material 66 whose solubility is dependent on borate ion concentration includes polyvinyl alcohol polymers, or copolymers wherein one polymer is polyvinyl alcohol, which gel in the presence of borate ions in aqueous solution, but which break down in the presence of large excesses of water as the borate ion diffuses away from the polymer and the borate ion concentration decreases.

One example of urine insoluble, water soluble material 66 whose solubility is dependent on salt sensitive binders includes nonwoven webs bound together with salt-sensitive binders. For example, some acrylic copolymers precipitate in the presence of high concentrations of calcium ions.

The absorbent assembly 50, positioned between the material 66 and the body side liner 48, can be any structure which is generally compressible, conformable, non-irritating to the child's skin, and capable of absorbing and retaining liquids and certain body wastes. The absorbent assembly 50 can be manufactured in a wide variety of sizes and shapes, and from a wide variety of liquid absorbent materials commonly used in the art. For example, the absorbent assembly 50 can suitably include a matrix of hydrophilic fibers, such as a web of cellulosic fluff, mixed with particles of a high-absorbency material commonly known as superabsorbent material. In a particular embodiment, the absorbent assembly 50 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 50 to better contain and absorb body exudates. The concentration of the superabsorbent particles can also vary through the thickness of the absorbent assembly 50. Alternatively, the absorbent assembly 50 can include a laminate of fibrous webs and superabsorbent material or other suitable means of maintaining a superabsorbent material in a localized area. Another type of absorbent material suitable for the absorbent assembly 50 is co-form, which is a blend of staple length and melt-blown fibers. The weight ratio of staple fibers to melt-blown fibers may range between 30 (staple)/70 (melt-blown) and 90 (staple)/10 (melt-blown). Wood pulp fibers are preferred for the staple fibers and polypropylene is preferred for the melt-blown fibers. Superabsorbent materials may be added to the co-form to increase capacity.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 50 is generally rectangular in shape, and includes a blend of wood pulp fluff and superabsorbent material. One preferred type of fluff is identified with the trade designation CR1654, available from U.S. Alliance, Childersburg, Ala., U.S.A., and is a bleached, highly absorbent sulfate wood pulp containing primarily soft wood fibers. As a general rule, the superabsorbent material is present in the absorbent assembly 50 in an amount of from about 0 to about 90 weight percent based on total weight of the absorbent assembly 50. The absorbent assembly 50 suitably has a density within the range of about 0.10 to about 0.35 grams per cubic centimeter. The absorbent assembly 50 may or may not be wrapped or encompassed by a suitable tissue wrap that maintains the integrity and/or shape of the absorbent assembly 50.

The outer cover 46 suitably includes a material that is substantially liquid impermeable, and can be elastic, stretchable or nonstretchable. The outer cover 46 can be a single layer of liquid impermeable material, but desirably includes a multi-layered laminate structure in which at least one of the layers is liquid impermeable. For instance, the outer cover 46 can include a liquid permeable outer layer 70 and a liquid impermeable inner layer 72 that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer 70 can be any suitable material and desirably one that provides a generally cloth-like texture. One example of such a material is a 20 gsm (grams per square meter) spunbond polypropylene nonwoven web. The outer layer 70 may also be made of those materials of which liquid permeable body side liner 48 is made. While it is not a necessity for the outer layer 70 to be liquid permeable, it is desired that it provides a relatively cloth-like texture to the wearer.

The inner layer 72 of the outer cover 46 can be both liquid and vapor impermeable, or can be liquid impermeable and vapor permeable. The inner layer 72 is desirably manufactured from a thin plastic film, although other flexible liquid impermeable materials may also be used. The inner layer 72, or the liquid impermeable outer cover 46 when a single layer, prevents waste material from wetting articles, such as car seats and clothing, as well as the wearer and caregiver. A suitable liquid impermeable film for use as a liquid impermeable inner layer 72, or a single layer liquid impermeable outer cover 46, is a 0.02 millimeter polyethylene film commercially available from Huntsman Packaging of Newport News, Va., U.S.A. If the outer cover 46 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 46. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

The liquid permeable body side liner 48 is illustrated as overlying the outer cover 46 and absorbent assembly 50 (FIG. 3), and may but need not have the same dimensions as the outer cover 46. The body side liner 48 is desirably compliant, soft feeling, and non-irritating to the child's skin. Further, the body side liner 48 can be less hydrophilic than the absorbent assembly 50, to present a relatively dry surface to the wearer and permit liquid to readily penetrate through its thickness.

The body side liner 48 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the body side liner 48. For example, the body side liner 48 can be composed of a meltblown or spunbonded web of polyolefin fibers. The body side liner 48 can also be a bonded-carded web composed of natural and/or synthetic fibers. The body side liner 48 can be composed of a substantially hydrophobic material, and the hydrophobic material can, optionally, be treated with a surfactant or otherwise processed to impart a desired level of wettability and hydrophilicity. For example, the material can be surface treated with about 0.28 weight percent of a surfactant commercially available from the Rohm and Haas Co. under the trade designation Triton X-102. The surfactant can be applied by any conventional means, such as spraying, printing, brush coating or the like. The surfactant can be applied to the entire body side liner 48 or can be selectively applied to particular sections of the body side liner 48, such as the medial section along the longitudinal centerline.

A suitable liquid permeable body side liner 48 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 46 and body side liner 48 can include elastomeric materials, it can be desirable in some embodiments for the composite structure to be generally inelastic, where the outer cover 46, the body side liner 48 and the absorbent assembly 50 include materials that are generally not elastomeric.

As noted previously, the illustrated training pant 20 can have front and back side panels 42 and 44 disposed on each side of the absorbent chassis 32 (FIGS. 1 and 3). These transversely opposed front side panels 42 and transversely opposed back side panels 44 can be permanently bonded to the composite structure 40 of the absorbent chassis 32 and can be permanently bonded to one another along corresponding sides. Alternatively, the front and back side panels 42, 44 can be releasably attached to one another by a fastening system 68. The side panels 42 and 44 may be attached to the composite structure 40 and/or to one another using attachment means known to those skilled in the art such as adhesive, thermal or ultrasonic bonding. The side panels 42 and 44 can also be formed as a portion of a component of the composite structure 40, such as the outer cover 46 or the body side liner 48.

Suitable elastic materials, as well as one described process of incorporating elastic side panels into an absorbent garment, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material includes a stretch-thermal laminate (STL), a neck-bonded laminated (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Mornian; and European Patent Application No. EP 0 217 032 published on Apr. 8, 1987 in the names of Taylor et al.; all of which are incorporated herein by reference. Alternatively, the side panel material may include other woven or nonwoven materials, such as those described above as being suitable for the outer cover 46 or body side liner 48, or stretchable but inelastic materials.

To further enhance containment and/or absorption of body exudates, the swimpant 20 can include waist elastic members 82 and/or leg elastic members 84, as are known to those skilled in the art (FIGS. 1–3). The waist elastic members 82 can be operatively joined to the outer cover 46 and/or to the body side liner 48, and can extend over part or all of the waist edges 38, 39. The leg elastic members 84 are desirably operatively joined to the outer cover 46 and/or to the body side liner 48 longitudinally along the opposite side edges 36 and positioned in the crotch region 26 of the swimpant 20.

The waist elastic members 82 and the leg elastic members 84 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the waist elastic members 82 and/or the leg elastic members 84 include a plurality of dry-spun coalesced multifilament spandex elastomeric threads sold under the trade name LYCRA® and available from E.I. du Pont de Nemours and Company, Wilmington, Del., U.S.A. In another particular embodiment, for example, the waist elastic members 82 and/or the leg elastic members 84 include Findley HX 2695-01 adhesive laminated to two facings of 0.6 osy (ounces per square yard) bicomponent polypropylene/polyethylene spunbond. Alternatively, several strands of 310 decitex LYCRA® may be also laminated at 250% elongation between the spunbond facings in addition to the Findley adhesive.

As described herein, the various components of the swimpant 20 can be integrally assembled together employing various types of suitable attachment means, such as adhesive, sonic and thermal bonds or combinations thereof. The resulting product is an absorbent swimwear garment 20 that provides uncompromised urine and bowel movement containment before swimming, but allows draining of excess water from the garment 20 after swimming without substantially altering bowel movement containment.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. An absorbent garment comprising:
   a chassis defining a waist opening and first and second leg openings;
   a crotch area in the chassis between the first and second leg openings; and
   a water drain in the chassis, wherein a drain opening is covered with a urine insoluble, swim water soluble material.

2. The absorbent garment of claim 1, wherein solubility of the urine insoluble, swim water soluble material is temperature dependent.

3. The absorbent garment of claim 2, wherein the urine insoluble, swim water soluble material is soluble in aqueous fluids below 25 degrees Celsius and insoluble in aqueous fluids above 25 degrees Celsius.

4. The absorbent garment of claim 1, wherein solubility of the urine insoluble, swim water soluble material is pH dependent.

5. The absorbent garment of claim 1, wherein solubility of the urine insoluble, swim water soluble material is dependent on enzyme catalysis.

6. The absorbent garment of claim 1, wherein solubility of the urine insoluble, swim water soluble material is dependent on borate ion concentration.

7. The absorbent garment of claim 1, wherein solubility of the urine insoluble, swim water soluble material is dependent on salt sensitive binders.

8. The absorbent garment of claim 1, wherein the urine insoluble, swim water soluble material is partially soluble in swim water.

9. The absorbent garment of claim 1, wherein the chassis comprises an outer cover, a body side liner, and an absorbent assembly between the outer cover and the body side liner.

10. The absorbent garment of claim 9, wherein the urine insoluble, swim water soluble material is located between the absorbent assembly and the outer cover.

11. The absorbent garment of claim 8, wherein the urine insoluble, swim water soluble material is located on an outer surface of the outer cover.

12. The absorbent garment of claim 1, wherein the water drain is located in the crotch area.

13. The absorbent garment of claim 1, wherein the drain opening comprises a plurality of openings in the crotch area of the outer cover.

14. Swimwear comprising the absorbent garment of claim 1.

15. An absorbent garment comprising:
   a chassis defining a waist opening and first and second leg openings;
   a crotch area in the chassis between the first and second leg openings;
   a pair of containment flaps adjacent the first and second leg openings in the crotch area; and
   a water drain in each of the containment flaps, wherein drain openings in the water drain are covered with a urine insoluble, swim water soluble material.

16. The absorbent garment of claim 15, wherein the drain openings in the containment flaps are covered with a spunbond material.

17. The absorbent garment of claim 15, wherein solubility of the urine insoluble, swim water soluble material is temperature dependent.

18. The absorbent garment of claim 17, wherein the urine insoluble, swim water soluble material is soluble in aqueous fluids below a specified temperature and insoluble in aqueous fluids above the specified temperature.

19. The absorbent garment of claim 18, wherein the specified temperature is about 25 degrees Celsius.

20. The absorbent garment of claim 15, wherein solubility of the urine insoluble, swim water soluble material is pH dependent.

21. The absorbent garment of claim 15, wherein solubility of the urine insoluble, swim water soluble material is dependent on enzyme catalysis.

22. The absorbent garment of claim 15, wherein solubility of the urine insoluble, swim water soluble material is dependent on borate ion concentration.

23. The absorbent garment of claim 15, wherein solubility of the urine insoluble, swim water soluble material is dependent on salt sensitive binders.

24. The absorbent garment of claim 15, wherein the drain openings comprise a plurality of openings in the containment flaps.

25. The absorbent garment of claim 15, wherein the urine insoluble, swim water soluble material is partially soluble in swim water.

26. Swimwear comprising the absorbent garment of claim 15.

27. An absorbent swimwear garment comprising:
   a chassis defining a waist opening and first and second leg openings, the chassis including at least a liquid-permeable body side liner, a substantially liquid-impermeable outer cover, and an absorbent assembly between the body side liner and the outer cover;
   a crotch area in the chassis between the first and second leg openings; and
   a water drain in the crotch area, wherein a drain opening in the water drain is covered with a urine insoluble, swim water soluble material.

28. The absorbent garment of claim 27, wherein solubility of the urine insoluble, swim water soluble material is temperature dependent.

29. The absorbent garment of claim 27, wherein the urine insoluble, swim water soluble material is soluble in aqueous fluids below a specified temperature and insoluble in aqueous fluids above a specified temperature.

30. The absorbent garment of claim 29, wherein the specified temperature is about 25 degrees Celsius.

31. The absorbent garment of claim 27, wherein solubility of the urine insoluble, swim water soluble material is pH dependent.

32. The absorbent garment of claim 27, wherein solubility of the urine insoluble, swim water soluble material is dependent on enzyme catalysis.

33. The absorbent garment of claim 27, wherein solubility of the urine insoluble, swim water soluble material is dependent on borate ion concentration.

34. The absorbent garment of claim 27, wherein solubility of the urine insoluble, swim water soluble material is dependent on salt sensitive binders.

35. The absorbent garment of claim 27, wherein the urine insoluble, swim water soluble material is located between the absorbent assembly and the outer cover.

36. The absorbent garment of claim 27, wherein the drain opening comprises a plurality of openings in the crotch area of the outer cover.

37. The absorbent garment of claim 27, further comprising a pair of containment flaps adjacent the first and second leg openings in the crotch area.

38. The absorbent garment of claim 37, wherein the drain opening comprises a plurality of openings in the containment flaps.

39. The absorbent garment of claim 27, wherein the urine insoluble, swim water soluble material is partially soluble in swim water.

40. Swimwear comprising the absorbent garment of claim 27.

* * * * *